United States Patent [19]

Barberet et al.

[11] Patent Number: Plant 6,271

[45] Date of Patent: Sep. 6, 1988

[54] CARNATION VARIETY 'LONDIBIS'

[75] Inventors: Nicole Barberet; Yves Ducloux, both of Antibes, France

[73] Assignee: Laboratoire de Physiologie Vegetale de la Londe, La Londe, France

[21] Appl. No.: 890,387

[22] Filed: Jul. 29, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A hybrid carnation cultivar particularly distinguished by its medium sized blooms having white petals which are marginally streaked with a dark red color providing an overall and distinctive red and white appearance, the blooms being carried singly on strong, upright stems of a medium length; the plant having a vigorous, upright and rather rigid growth habit with moderately abundant foliage, an average height of about eight-six centimeters at eight months and with a recurrent and profuse production of blooms.

1 Drawing Sheet

BACKGROUND OF THE NEW PLANT

This new carnation cultivar originated as a seedling selected from a group of seedlings produced by our crossing of selected and individually identified plants from among our stock of plants maintained at La Londe, Les Maures, France, for breeding purposes. This particular seedling was selected by us for propagation and test because of its very unusual white and red flower coloration and its apparently very favorable growth habit. This selected seedling was reproduced by us at La Londe by means of cuttings with very favorable results, which caused us to direct continued propagation of this new plant through several successive genrations, each generation being produced by cuttings from a parent generation and this work demonstrated clearly that the novel and distinctive characteristics of the originally selected seedling were fully retained from generation to generation and appeared to be firmly fixed.

DESCRIPTION OF THE DRAWING

This new carnation cultivar is illustrated by the accompanying photographic drawing which shows, in full color, several blooms in various stages from newly opened bud to fully opened bloom, the colors shown being as nearly true to those specified herein as is reasonably possible to obtain by conventional photographic procedures.

DESCRIPTION OF THE NEW PLANT

The following is a detailed description of our new carnation based upon observations of greenhouse grown plants made at La Londe, Les Maures, France, in early 1986, the color designations being specified according to The R.H.S. Colour Chart published by The Royal Horticultural Society at London, England.

THE PLANT

Origin: Seedling.

Parentage:

*Seed parent.*—Stock Plant No. 76 P 11.

*Pollen parent.*—Stock Plant No. 92 88 OR. These parent varieties are unnamed and unpatented and each is identified in our permanent records maintained at La Londe, France.

Classification:

*Botanic.*—Hybrid *Dianthus caryophyllus.*

*Commercial.*—Standard Carnation.

Form: An erect bush of medium height and comprising at least four stems emitted from a main stem near the ground.

Height: Average; about 87 cm. at eight months.

Main stem:

*Length.*—Less than 15 cm. owing to pinching.

Growth habit: Vigorous, upright and rather rigid.

Foliage:

*Quantity.*—Moderately abundant.

*Number of leaves.*—More than 120.

*Size of leaf.*—About 12.2 cm. in length and about 1.1 cm. in width (at the seventh node).

*Shape.*—Linear with rolled margins and acuminate tip.

*Texture.*—Leathery.

*Color.*—Upper side — 189A and 189B. Under side — 189A and 189B.

*Ribs, veins and rachis.*—Hardly noticeable.

THE BUD

Form: Ball shaped.

Size:

*Diameter.*—Averages about 2.2 cm.

*Length.*—Averages about 2.8 cm.

Rate of opening: Normal for carnations.

Color of petals:

*When sepals first divide.*—155D and 45D.

*When petals begin to unfurl.*—155D and 45C-D.

Sepals:

*Number.*—Five. The sepals are joined at the lower part and the upper part is of ovate character with sharp pointed apex. The sepals are hooded over the bud before dividing and stand up when the flowers open.

*Color.*—Inside — 145D. Outside — 191A-B.

Calyx:

*Shape.*—Funnel shaped.

*Size.*—Medium.

*Splitting.*—Sometimes the calyx splits.

*Aspect.*—Smooth.

Flower stem:

*Length.*—Averages about 56.5 cm.
*Character.*—Erect and rather rigid.
*Color.*—189B.

THE FLOWER

Blooming habit: Recurrent and profusely during spring, midseason and fall with a tendency to give fewer blooms in fall.
Size of bloom: Medium.
*Diameter.*—Averages about 8 cm.
*Depth.*—Averages about 5.2 cm.
Borne: Singly.
Shape:
*When bloom first opens.*—Flat.
*When bloom matures.*—High centered.
Petalage:
*Number of petals.*—Averages about 72.
*Arrangement.*—Imbricated.
*Form.*—Fan shaped with rounded edges and finely serrated apex edges.
*Texture.*—Soft.
*Appearance.*—Shiny.
*Color.*—Both outer and inside petals: Top side: Body — Mainly 155D with streaks of 45C and 45D at the apex margin. Base — Greenish. Reverse side — 155D with streaks of 45D at apex margin.
Petaloids:
*Number.*—Less than eight.
*Size.*—Smaller than the petals.
*Color.*—Same as the petals.
Flower stem:

*Length.*—Averages about 56.5 cm. when cut at tenth node.
*Character.*—Upright and of good strength.
Fragrance: Perceptible.
Persistence: The petals hang on and dry.
Disease resistance: Very resistant to *Fusarium oxysporum* as observed I.N.R.A. Antibes, France.
Lasting quality:
*As a cut flower.*—At least ten days in vase keeping.

REPRODUCTIVE ORGANS

Stamens:
*Number.*—4 to 14.
*Arrangement.*—Around the ovary.
*Anthers.*—Size: Less than 0.4 cm. Color: Whitish.
*Filaments.*—Length: Averages about 1.6 cm. Color: Whitish.
Pistils:
*Number.*—3 or 4.
*Styles.*—Length: Averages about 1.7 cm. Color: Whitish.
*Stigmas.*—Color: Pinkish.
Character of ovary: The ovary is ribbed.

We claim:

1. The new and distinct carnation cultivar, substantially as herein shown and described, characterized by the flower petals being overall white and streaked with dark red at the outer end margins, the flowers being of medium size and produced profusely during the recurrent blooming periods of the plant, the plant itself being of medium height and the flower stem being long and of good strength.

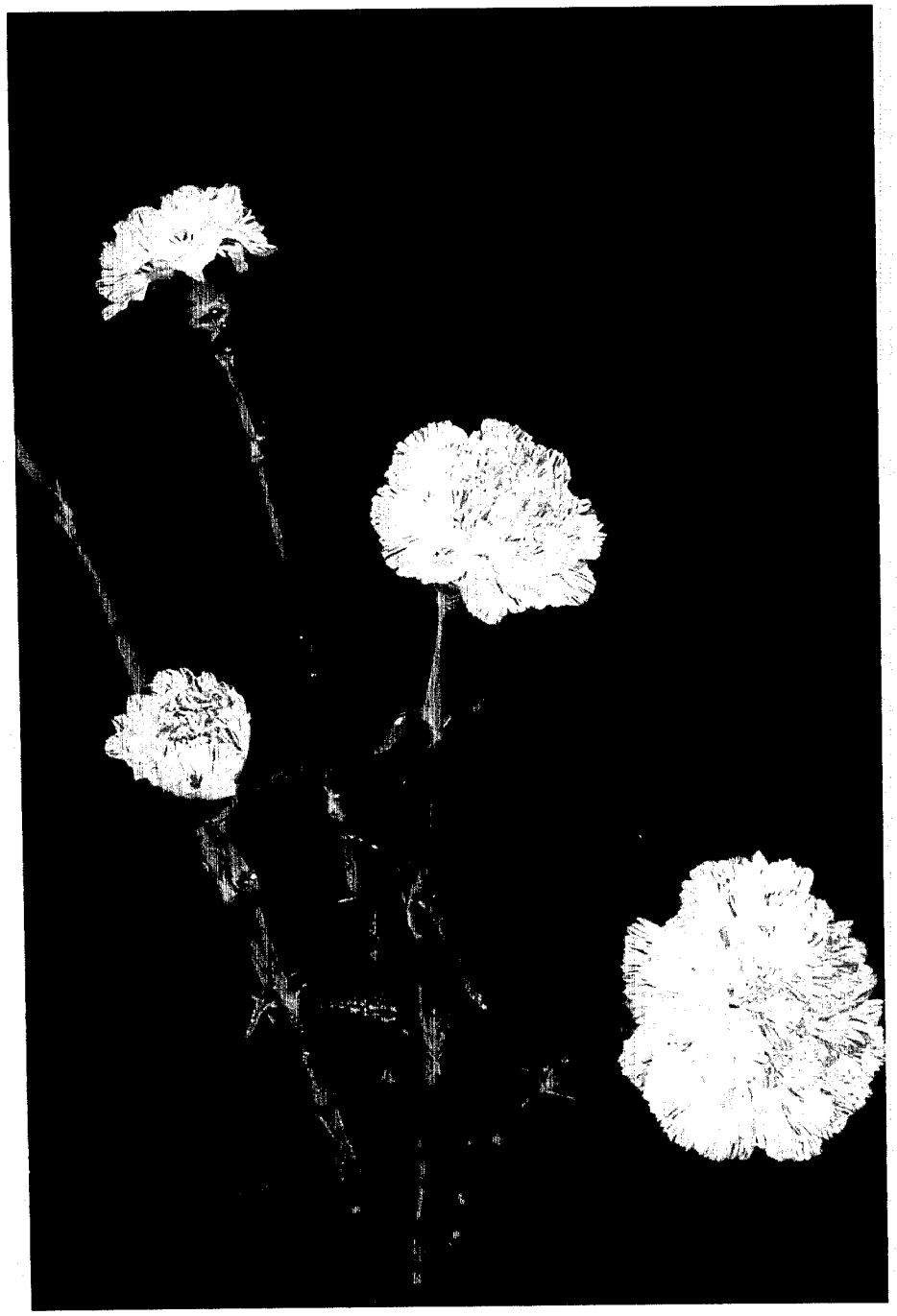

* * * * *